United States Patent [19]
Chu et al.

[11] Patent Number: 5,549,796
[45] Date of Patent: Aug. 27, 1996

[54] ELECTROPHORESIS USING CONTOUR-CLAMPED ELECTRIC FIELDS

[75] Inventors: Gilbert Chu, Palo Alto; Douglas Vollrath, Mountain View; Ron Davis, Palo Alto, all of Calif.

[73] Assignee: The Board of Trustees of the Leland Stanford Junior University, Stanford, Calif.

[21] Appl. No.: 241,063

[22] Filed: May 11, 1994

Related U.S. Application Data

[63] Continuation of Ser. No. 949,762, Sep. 23, 1992, abandoned, which is a continuation of Ser. No. 691,637, Apr. 25, 1991, abandoned, which is a continuation of Ser. No. 235,296, Aug. 23, 1988, Pat. No. 5,165,898, which is a continuation-in-part of Ser. No. 896,526, Aug. 14, 1986, abandoned.

[51] Int. Cl.⁶ .......................... G01N 27/26; G01N 27/447
[52] U.S. Cl. .......................... 204/457; 204/466; 204/608; 204/620
[58] Field of Search .......................... 204/299 R, 182.8

[56] References Cited

U.S. PATENT DOCUMENTS

| | | | |
|---|---|---|---|
| 4,148,703 | 4/1979 | Trop | 204/182.1 |
| 4,315,812 | 2/1982 | Karlson | 204/299 R |
| 4,371,746 | 2/1983 | Pepper, Jr. | 178/18 |
| 4,473,452 | 9/1984 | Cantor et al. | 204/182.8 |
| 4,670,119 | 6/1987 | Hurd | 204/182.3 |
| 4,878,008 | 10/1931 | Ragsdale | 323/271 |
| 4,911,817 | 3/1990 | Kindlmann | 204/299 R |

FOREIGN PATENT DOCUMENTS

| | | |
|---|---|---|
| 0256737 | 2/1988 | European Pat. Off. . |
| 307332A | 3/1989 | European Pat. Off. . |
| 307332A2 | 3/1989 | European Pat. Off. . |
| 0356187 | 2/1990 | European Pat. Off. . |
| 60-242358 | 2/1985 | Japan . |
| WO84/02001 | 5/1984 | WIPO . |

OTHER PUBLICATIONS

Clark et al., "A Novel Instrument for Separating Large DNA Molecules with Pulsed . . . , " Science, vol. 241 (1988), pp. 1203–1205.

Sobral et al., "Pulse Time and Agarose Concentration Affect the Electrophoretic . . . , " Nucleic Acids Research, vol. 17, No. 18 (1989), pp. 7359–7369.

Chu, "Pulsed Field Electrophoresis in Contour–Clamped Homogenous . . . , " Electrophoresis, vol. 10 (1989), pp. 290–295.

Chu, "Pulsed–Field Gel Electrophoresis: Theory and Practice," Methods: A Comparison to Methods in Enzymology, vol. 1, No. 2 (1990), pp. 129–142.

Cantor et al., "Voltage Ramp Pulsed Field Gel Electrophoresis Separation of Large DNA Molecules," *Electrophoresis 1986, Proceeding of the Fifth Meeting of the International Electrophoresis Society*, M. J. Dunn ed., (1986) pp. 161–171.

Schwartz et al., "Separation of Yeast Chromosome–Sized DNAs by Pulsed Field Gradient Gel Electrophoresis," *Cell*, 37 (1984), pp. 67–75.

(List continued on next page.)

*Primary Examiner*—John Niebling
*Assistant Examiner*—John S. Starsiak, Jr.
*Attorney, Agent, or Firm*—Majestic, Parsons, Siebert & Hsue

[57] ABSTRACT

A gel electrophoresis method and apparatus is described in which the shape and orientation of the electric field is controlled by contour clamping. Electrodes are arranged around a closed contour. Two or more electrodes, the driving electrodes, are clamped at a potential difference $\phi_0$ to establish the general orientation and strength of the electric field. The remaining electrodes are clamped to intermediate potentials to control the shape of the field established by the driving electrodes. The field is varied in accordance with the purpose of the electrophoresis, depending upon the size of the particles and the information to be determined concerning the particles.

28 Claims, 12 Drawing Sheets

OTHER PUBLICATIONS

Carle et al., "Separation of Chromosomal DNA Molecules From Yeast by Orthogonal–Field–Alternation Gel Electrophoresis," *Nucleic Acids Research,* 12:14 (1984), pp. 5647–5564.

Carle et al., "Electrophoretic Separations of Large DNA Molecules by Periodic Inversion of the Electric Field," *Science,* 232 (1986), pp. 65–68.

Lumpkin et al., "Theory of Gel Electrophoresis of DNA," *Biopolymers,* 24 (1985), pp. 1573–1593.

Carle et al., "An Electrophoretic Karyotype for Yeast," *Proc. Nat. Acad. Sci. USA,* 82 (1985), pp. 3756–3760.

Kemp et al., "Size Variation in Chromosomes From Independent Cultured Isolates of *Plasmodium falciparum,*" *Nature,* 315 (1985), pp. 347–350.

Schwartz et al., "New Techniques for Purifying Large DNA's and Studying Their Properties and Packaging," *Cold Spring Harbor Symp. Quant. Biol,* 47 (1983) pp. 189–195.

Van der Ploeg et al., "Antigenic Variation in *Trypanosoma brucei* Analyzed by Electrophoretic Separation of Chromosome–Sized DNA Molecules," *Cell,* 37 (1984) pp. 77–84.

Van der Ploeg et al., "Chromosome–Sized DNA Molecules of *Plasmodium falciparum,*" *Science,* vol. 229, (1985), pp. 658–661.

Fangman, "Separation of Very Large DNA Molecules by Gel Electrophoresis," *Nucleic Acids Research,* vol. 5, No. 3, (1978), pp. 653–665.

Spithill et al., "The Molecular Karyotype of *Leishmania major* and Mapping of $\alpha$ and $\beta$ Tubulin Gene Families to Multiple Unlinked *Chromosomal loci,*" *Nucleic Acids Research,* vol. 13, No. 11, (1985), pp. 4155–4169.

Birren et al., "Optimized Conditions for Pulsed Field Gel Electrophoretic Separations of DNA," *Nucleic Acids Research,* vol. 16, No. 15, (1988), pp. 7563–7580.

Gilbert Chu et al., *Science* "Separation of Large DNA Molecules by Contour–Clamped Homogeneous Electric Fields" (1986) 234:1582–1585.

5,549,796

ELECTROPHORESIS USING CONTOUR-CLAMPED ELECTRIC FIELDS

This is a continuation of application Ser. No. 07/691,637, filed Apr. 25, 1991, now abandoned which is a continuation of application Ser. No. 07/235,296, filed Aug. 23, 1988, now U.S. Pat. No. 5,165,898, which is a continuation-in-part of application Ser. No. 06/896,526, filed Aug. 13, 1986, now abandoned.

INTRODUCTION

This invention is in the field of gel electrophoresis and pertains to a method and apparatus for controlling the migration of particles by manipulating the shape and orientation of the electric field in the gel.

BACKGROUND

Gel electrophoresis is capable of separating macromolecules such as proteins and nucleic acids on the basis of size, charge, and/or conformation. Most applications involve the use of a single pair of electrodes to generate the electric field. Such a field is necessarily constrained to be uniform and oriented in a single direction, and as a result conventional techniques are limited in many respects.

For example, conventional electrophoresis is not capable of resolving DNA fragments much larger than 50 kilobases. The recent introduction of new electrode configurations which generate electric fields in alternating orientations has allowed the separation of large DNA molecules up to 2 megabases in size. For example, U.S. Pat. No. 4,473,452 describes an electrophoresis method of separating DNA molecules which involves the use of electric fields deliberately chosen to be nonuniform, rather than the uniform fields sought in previously known electrophoresis methods. The nonuniformity of the electric field, however, causes the DNA molecules to migrate with a mobility and a trajectory that depends on where in the gel the sample is loaded. Thus, comparison of multiple samples across the gel is difficult.

For example, conventional electrophoresis may produce distortion, with molecules at the edge of the gel migrating more slowly than those in the center. Consequently electrophoresis is often done inefficiently at voltages lower than necessary to achieve adequate resolution.

For example, conventional electrophoresis is limited in resolution by band broadening.

Also, conventional electrophoresis is not capable of identifying macromolecules with different secondary structure. Two dimensional electrophoresis has been developed for this purpose, but this method is technically difficult because it involves manipulations of the gel.

SUMMARY

It is a principle object of the present invention to provide a method for manipulating the shape and orientation of electric fields for the purpose of controlling the migration of particles in a gel.

It is another object of the present invention to provide for the high resolution separation of macromolecules, particularly DNA molecules up to or greater than 2 megabases in size, by gel electrophoresis whereby the pattern of separation is independent of position in the gel.

It is a further object of this invention to provide a means for separating relatively small macromolecules, such as DNA of less than 50 kilobases, without distortion even at high voltage.

Yet another object of the present invention is to minimize band broadening in the electrophoretic separation of macromolecules.

A still further object of this invention is to provide a method for identifying secondary structure in macromolecules.

These and other advantages of the invention, as well as additional inventive features, will become apparent from the detailed description which follows.

The present invention is predicated in part on the discovery that the limitations inherent in the existing electrophoretic separation techniques can be overcome by applying contour-clamped uniform or nonuniform electric fields, with the term "contour-clamped electric field" meaning that the electric field is generated by multiple electrodes arranged along a closed contour clamped to predetermined electric potentials, and with the term "uniform electric field" meaning an electric field having a uniform direction and magnitude within a closed contour.

Depending upon the particular application for the method and apparatus, the gel is subjected to a uniform or nonuniform field by clamping a plurality of electrodes at predetermined potentials, where at least two electrodes clamped to different potentials serve as the driving electrodes and at least two more electrodes clamped to intermediate potentials serve to further define the nature of the electrical field.

One significant application is the separation of large macromolecules employing a uniform field. The driving electrodes are clamped at potentials $\phi_1$ and $\phi_2$ corresponding to a potential difference of $\phi_0 = \phi_2 - \phi_1$.

The remaining electrodes located at intermediate positions along the polygon are clamped to intermediate potentials as determined by the equation:

$$\phi = \frac{y_n}{a}(\phi_2 - \phi_1) + \phi_1$$

where "$\phi_1$" and "$\phi_2$" are the potentials of the driving electrodes with $\phi_1$ being the lower potential; "a" represents the perpendicular distance between opposing driving electrodes (i.e. in a direction normal to the $\phi_1$ electrodes); and "$Y_n$" represents the perpendicular distance between the nth intermediate electrode and the $\phi_1$ electrodes. Thus, positions along the closed contour are clamped to potentials equal to those that correspond to a uniform electric field. While an infinite number of electrodes would need to be arranged along the contour to provide an exactly uniform electric field inside the contour, as a practical matter and as demonstrated herein, a relatively small number of electrodes can generate an excellent approximation of the desired uniform field.

DETAILED DESCRIPTION

Figure 1:
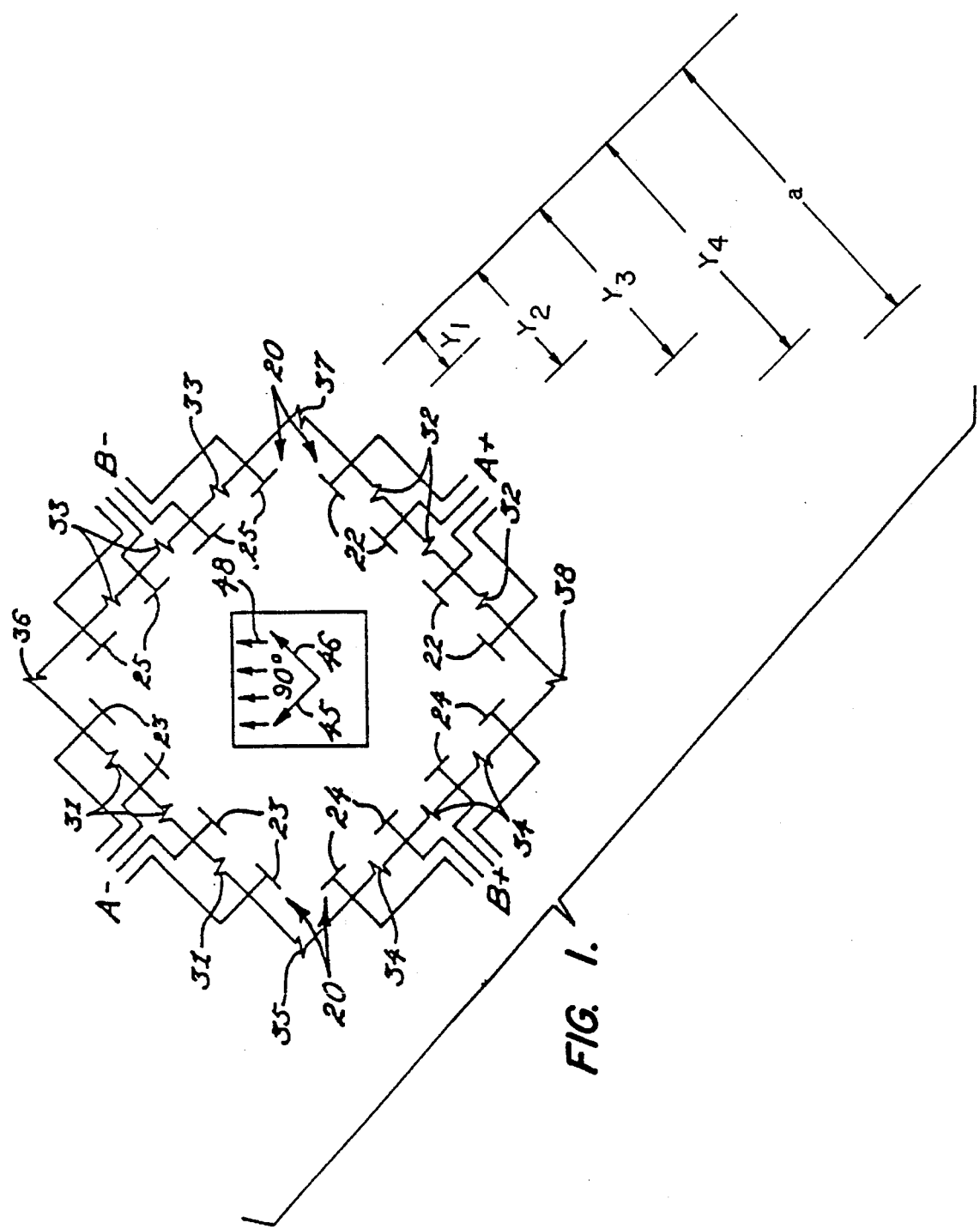
FIG. 1 depicts the apparatus of the present invention for the square array alternating contour-clamped homogenous electric field.

While the invention will be described in connection with certain embodiments, it is not intended to limit the invention to those particular embodiments. On the contrary, it is intended to cover all alternatives, modifications, and equivalent arrangements as may be included within the spirit and scope of the invention as defined by the appended claims.

The present inventive method for identifying particles comprises subjecting the particles in a suitable medium to an electric field generated by electrodes arranged along a two-dimensional closed contour having at least two electrodes or groups of electrodes which serve as driving electrodes. Normally, the contour is polygonal and has at least two parallel sides. The driving electrodes have a potential difference $\phi_0$ imposed across them and determine the general direction of the electric field. The remaining electrodes, which are located at intermediate positions between the driving electrodes, have intermediate potentials adjusted to make the electric field either uniform or nonuniform, as desired. The thus-clamped field more effectively controls the migration of the particles, providing for improved resolution, information concerning secondary structure, as well as other advantages.

By emphasizing contour-clamped electric fields which allow for controlling and varying the shape of the electric field in the gel, substantial versatility is achieved. The contour-clamped electric field may be employed in combination with alternating fields to further expand the application of the contour-clamped electric field. By emphasizing combinations of uniform or nonuniform electric fields with alternating or non-alternating electric fields, various results can be achieved at levels superior to what presently available gel electrophoretic equipment provides. By employing a combination of a uniform electric field and alternating the uniform field, separation of very large nucleic acids can be achieved, e.g. separation of large DNA of up to and greater than 2 megabases. For separation of medium to small DNA molecules, e.g. equal to or less than about 50 kbp, a uniform non-alternating field provides rapid separation with high resolution. Where a uniform alternating field is employed, but the alternating fields are different field strengths, the particle migration may be related to secondary structure. With a non-alternating nonuniform field, differential resolution and/or decreased band broadening may be accomplished. Other variations with the combination of a contour-clamped electric field and alternating/non-alternating fields may also be employed for modifying the resolution, migration path and rate of separation.

When employing the term "particle", any substance capable of migrating in a gel under the influence of an electric field is intended. Thus, the particle includes both large and small molecules, from amino acids and nucleotides to large proteins and nucleic acids, e.g. chromosomes.

While for the most part, the electrodes will define a polygonal contour, such a regular two-dimensional electrode array is not required and the closed-contour may have any regular or irregular shape. However, for convenience, a square, rectangular or hexagonal array will be used, and these polygons will serve as paradigmatic of other regular or irregular polygons.

Electrophoresis can be used for a variety of purposes, such as identifying a particle by size, charge, conformation or combinations thereof, for separating a mixture of particles, purification of particles, or the like. The electrophoresis is carried out in a gel conventionally prepared using agarose or polyacrylamide as the gelling agent, although other gelling agents may find use.

In carrying out the method of the subject invention an electric field of a desired shape is created in the gel. The field is maintained during the electrophoresis and may be uniform or nonuniform, alternating or nonalternating, where the angle between the two directions will normally be 60° or greater and may be 90°, 120°, or other angles. The gel is supported in a reservoir containing a buffered medium and located within the closed contour of the electrode array. One or more samples are loaded near one end of the gel. The gel is positioned within the electrode array to provide the proper migration direction for the particle(s). For the most part, gels will be rectangular.

The field is applied to the gel, where the buffered medium may be circulated and cooled. The field is maintained for a sufficient time to ensure the desired migration distance of the particle(s) to obtain at least sufficient resolution of the particles.

The first embodiment of the subject invention to be discussed is the uniform field with alternating electric fields of either the same or different field strength.

The electrophoretic separation of large macromolecules, such as DNA chromosomes of up to at least 2 megabases, is most efficiently made using a contour-clamped homogenous electric field in alternating orientations.

Figure 2:
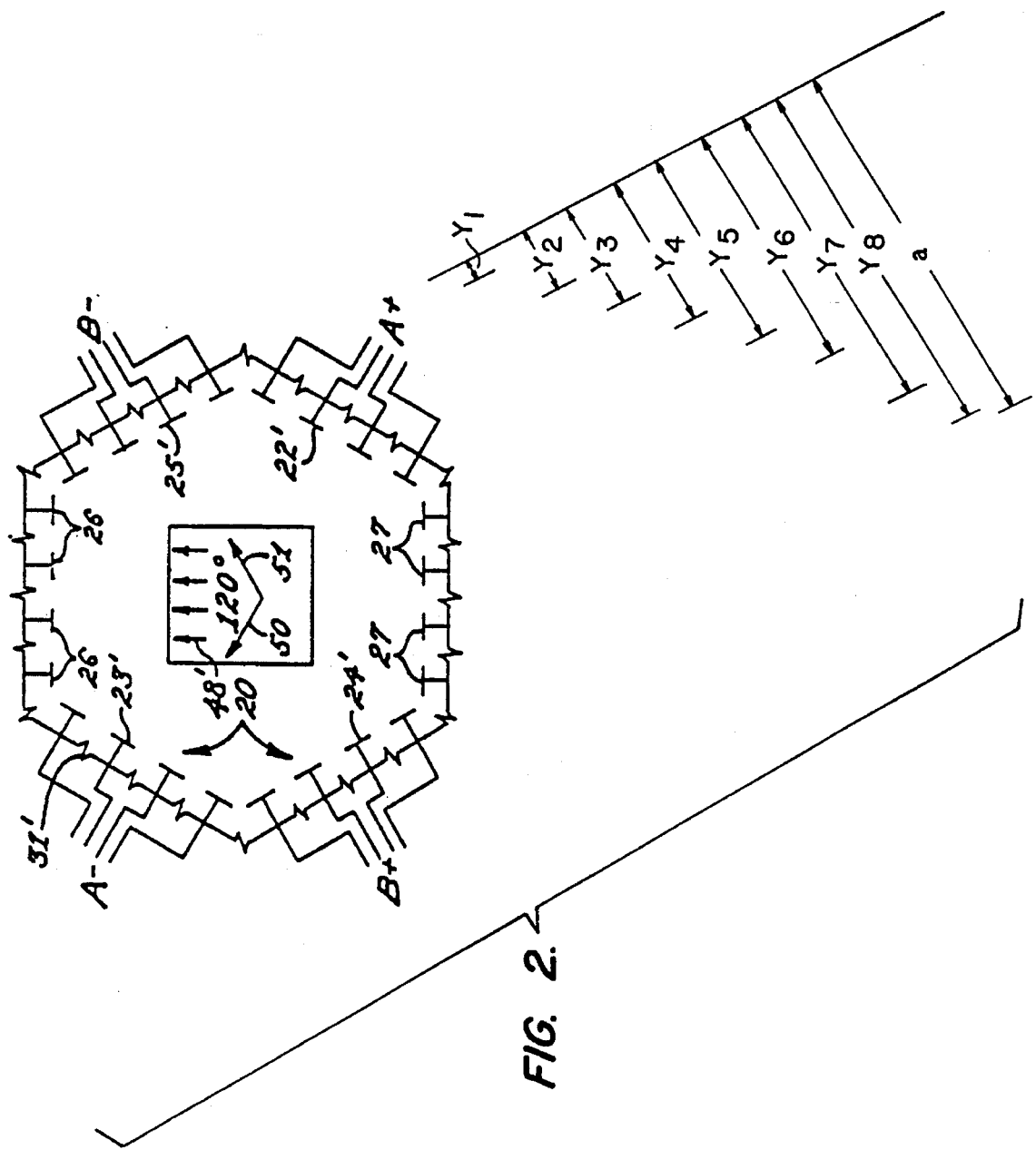
FIG. 2 shows the apparatus for the hexagonal array alternating contour-clamped homogenous electric field.

Two exemplary devices useful in explaining certain principles of the invention are illustrated in FIGS. 1 and 2. Both devices apply a contour-clamped homogenous electric field alternating between two directions by virtue of the location of a series of electrodes generally indicated at 20. As is apparent from the drawings, the contours of both devices are closed, the FIG. 1 device in the form of a square and the FIG. 2 device in the form of a hexagon. As already indicated, the polygonal contour, however, need not be a square or hexagon; indeed, electrodes arranged along other contours can be used so long as the multiple electrodes are arranged on a closed contour, have at least a pair of parallel sides, and are clamped to appropriate potentials.

Figure 8:
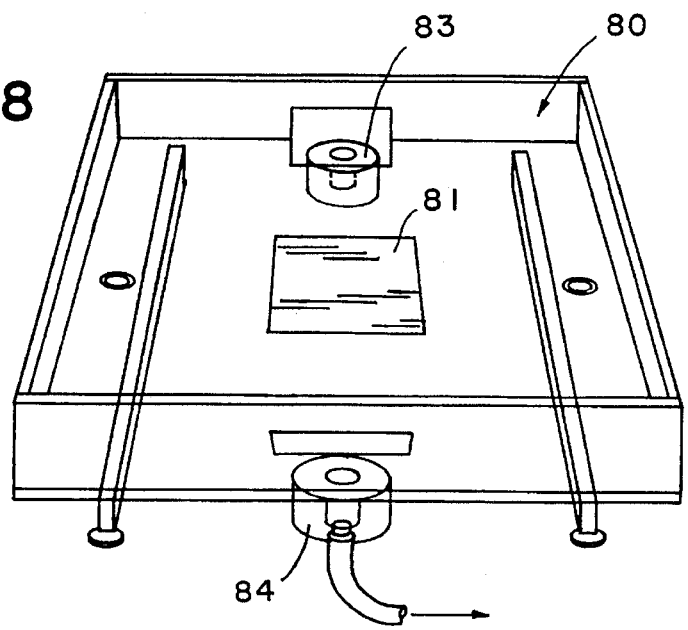
FIG. 8 depicts one embodiment of this invention including circulating and cooling means.

The structure of the apparatus used in the present invention will become more apparent by closer reference to FIG. 1. The electrodes 20 are suspended in a buffer tank (not shown) and immersed in a buffer solution. The buffer solution can be circulated and cooled in conventional fashion. A sample holder, such as a sandblasted glass plate 21 is positioned in the buffer tank in the illustrated position so that the direction of travel of the chromosomes will be parallel to the plate edges. The gel is deposited on the surface of the sample holder 21, and inserts containing the molecules to be separated are loaded into wells formed in the gel. As shown in FIG. 8, one embodiment includes a buffer tank 80 including sample 81, and inlet means 83 and outlet means 84 circulating the buffer solution via a suitable pump (not shown). If desired, the buffer solution can be cooled using a suitable cooling means (not shown).

Electrodes 20 are preferably equally spaced as illustrated and positioned around the closed contour within which the field is to be created. They can be formed, for example, of 0.030 inch diameter platinum wire and as noted above are suspended in the buffer solution. The electrodes may be point or line sources positioned in the plane of or normal to the plane of movement of the nucleic acids. The electrodes of the FIG. 1 embodiment can be considered as two pairs, the electrodes 22, 23 forming what can be considered the A pair, and the electrodes 24, 25 comprising the B pair.

The electrodes may be positioned in a variety of ways, displaced from the gel or abutting the gel. Usually, for alternating fields, the electrodes will be displaced from the gel with the interelectrode distances desirably being less than the distance of the electrodes from the gel.

In accordance with the invention, one of the pairs, such as the A pair, is energized or clamped to a potential difference $\phi_0$, while the other pair, such as the B pair, serves as intermediate electrodes which are clamped to potentials which control the uniformity of the field between the first pair. The FIG. 1 embodiment is arranged to alternate the field between two orientations. When it is desired to alternate between the condition just described and its alternate, the B pair is clamped to the potential difference $\phi_0$ while the A pair serves as intermediate electrodes which are clamped at intermediate potentials to assure the uniformity of the field created between the B pair.

The manner in which that is accomplished will now be described. First of all, it is seen that each electrode, in addition to being connected to its A or B supply, is also connected to its neighbors by a resistor. Resistors 31 interconnect the A− electrodes, resistors 32 the A+ electrodes, resistors 33 the B− electrodes, and resistors 34 the B+ electrodes. In addition, resistors 35, 36, 37 and 38 interconnect the respective A pairs and B pairs as illustrated.

Figure 3:
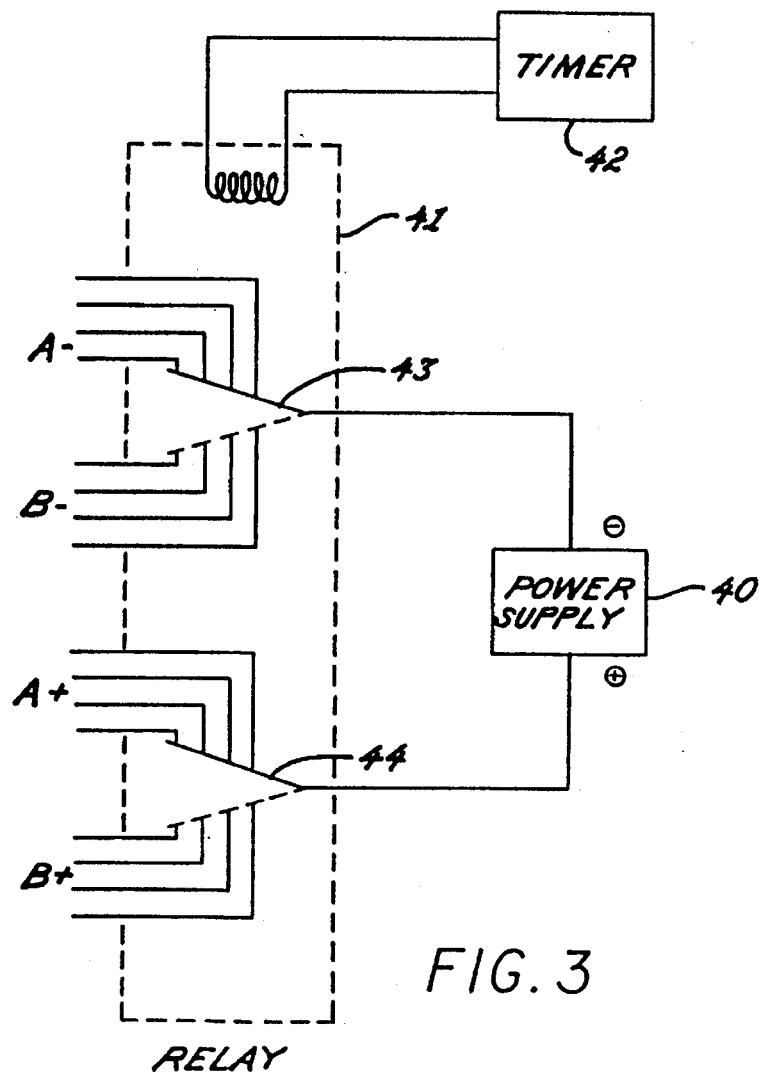
FIG. 3 shows a switching power supply for connection to the electrodes of the apparatus of FIGS. 1 and 2.

For applying potentials to the electrodes, a switched power supply illustrated in FIG. 3 is connected to the electrodes corresponding to the A and B designations. The switched power supply includes power supply 40 having positive and negative terminals connected to a relay, preferably an electronic relay, schematically illustrated at 41. The relay is driven by a timer 42 which controls the conducting or nonconducting state of a series of electronic switches which in turn are connected to the electrodes of FIGS. 1 or 2. For the sake of simplicity, the relay is illustrated as a mechanical relay, but the manner in which appropriate shift registers, diodes and power transistors are to be configured will be apparent from the following description. It is seen that the negative terminal of the power supply is connected to a switch 43 which, in the solid line position, connects the negative terminal to the A− electrodes and in the alternate dashed line position connects the negative terminal to the B− electrodes. Similarly, the positive terminal of the power supply is connected to a switch 44 which in the illustrated solid line position connects the positive terminal to the A+ electrodes and in the alternate dashed line position connects the positive terminal of the power supply to the B+ electrodes. The timer 42 causes the contacts to switch positions at predetermined intervals such as, for example, in the range of about 20 to 200 seconds.

With the terminals in the illustrated position, the potential difference from the power supply, designated $\phi_0$ herein, is applied to the A+ to the A− electrodes creating a field in the direction illustrated by the arrow 45. Thus, the A set of terminals has the potential $\phi_0$ imposed thereacross to create a field in the illustrated direction. For the purpose of making the field uniform, the B terminals serve as intermediate electrodes by virtue of their connection across the A electrodes by the resistors 36, 33 and 37 for the B− set and 35, 34 and 38 for the B+ set. In one configuration, the resistors used were each of 820 ohms, 2 watts, and each intermediate electrode was therefore clamped to the appropriate potential which caused the field between the A+ and A− electrodes to be of substantially uniform value throughout the area encompassed by the electrodes. When it is desired to switch the direction of the field, the timer 42 (FIG. 3) causes the switches 43, 44 to switch to their alternate position at which point the B set of electrodes is clamped to the potential difference $\phi_0$ whereas the A set of electrodes, by virtue of their intermediate resistors, serve as the intermediate electrodes to make the field uniform in the direction 46 created between the B pair of electrodes.

It is known that periodic alternation of the field direction serves to separate particles or molecules larger in size than those capable of being separated without alternation. For example, Cantor et al. U.S. Pat. No. 4,473,452 describes a square array using an alternating field. However, the field is created between a single electrode on one side of the sample and a linear array of electrodes on the other. Thus, different parts of the gel are subjected to different reorientation angles by virtue of the gradient created between the single electrode on one side and the array on the other.

In accordance with the present invention, there is no gradient. In other words, the field is uniform between the electrodes clamped at the potential difference $\phi_0$. Thus, in the square array of FIG. 1 when the field alternates between the A pair and the B pair, the entire gel is subjected to a reorientation angle of 90° independent of position. As a result, all positively changed molecules are caused to move in the direction which bisects the 90° reorientation angle, as illustrated by the set of equal size arrows 48. Nucleic acids having a negative charge would move in the opposite direction.

With the 90° reorientation angle there is relatively quick movement of DNA down the gel together with a loss of resolution. However, when the reorientation angle is increased to 120°, it is possible to obtain excellent resolution of DNA over the entire range of sizes encountered, extending up to two megabases, with either fragmented or intact DNA molecules.

Accordingly, the apparatus of FIG. 2 is configured to provide a reorientation angle of 120°. In FIG. 2, it is seen that the closed contour is in the form of a hexagon and opposed sets of equally spaced electrodes are disposed on each side of the hexagon. There is illustrated an A set of electrodes 22', 23', a B set 24', 25', and an additional set 26, 27. As in the FIG. 1 embodiment, resistors (e.g., resistor 31') are connected between each pair of adjacent electrodes to close the contour. In the FIG. 2 embodiment, resistors of 470 ohms, 2 watts, were used. The arrows 48' indicate the direction of travel of positive particles. Nucleic acids or other negatively charged particles migrate in the opposite direction.

When the A set of electrodes is clamped at the potential difference $\phi_0$, the field is in the direction illustrated by arrow 50. In that condition, all of the electrodes 24', 25', 26, 27 act as intermediate electrodes to make the field established between the A pair of electrodes more uniform. Similarly, when the power supply of FIG. 3 switches to clamp the B pair of electrodes at potential difference $\phi_0$, the A pair as well as the additional pair 26, 27 all act as intermediate electrodes clamped at potentials suitable to make the field between the B electrodes, the direction of which is illustrated by the arrow 51, more uniform. The FIG. 2 configuration has the advantage over the FIG. 1 configuration of additional intermediate electrodes, providing eight in the illustrated embodiment as opposed to the four shown in the FIG. 1 embodiment.

Figure 4:
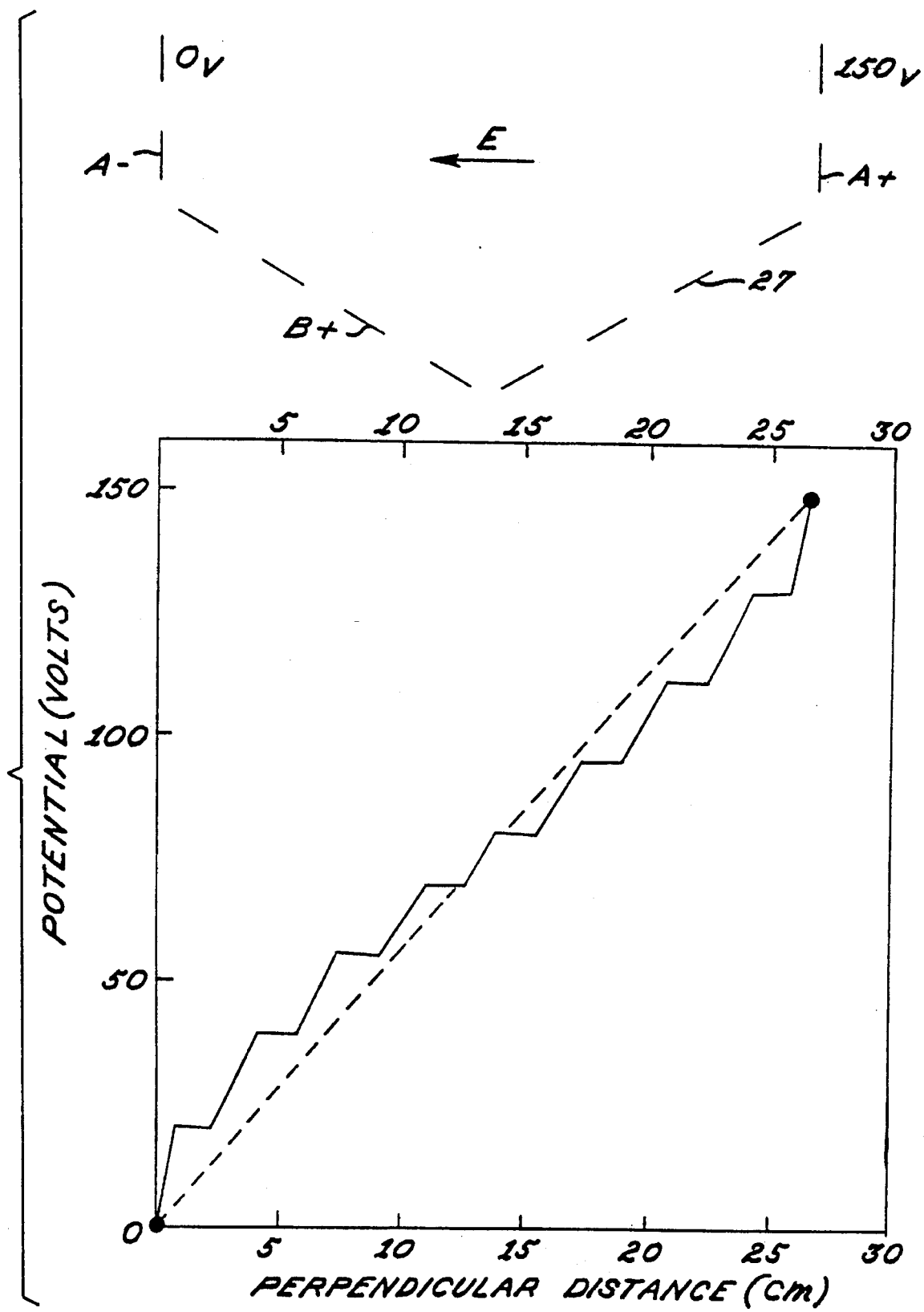
FIG. 4 is a graph showing the electric potential as a function of position in the hexagonal array contour-clamped homogenous electric field.

Referring briefly to FIG. 4, the uniformity of the field thus achieved is illustrated. FIG. 4 shows the potential (in volts) as a function of the perpendicular distance to the $\phi_1$ electrodes in the embodiment of FIG. 2 (i.e. normal to the $\phi_1$ electrodes).

At the upper portion of FIG. 4, there are schematically illustrated the electrodes, assuming that the A pair has $\phi_0$ clamped thereacross, $\phi_0$ being 150 volts in this instance. In that case, the B+ electrodes 24' and the additional electrodes 27 act as intermediate electrodes to make the field more uniform. Thus it is seen, referring to the graph that at the A+ electrode the potential is indeed 150 volts and at the A− electrode the potential is zero volts. The sawtooth line joining those two points illustrates the effect achieved by the device in practice. The dashed line shows the ideal potential profile for a completely uniform electric field. It is apparent that with only eight intermediate electrodes the ideal is approached quite closely, as will be apparent from inspection of the results achieved by the present invention.

The pattern of chromosome separation changes dramatically with the reorientation angle of the electric field. In the Carle and Olson apparatus, different parts of the gel are subjected to different reorientation angles, mostly in the range of 120° to 150°. In the hexagonal array, the angle is 120°, and in the square array, it is 90°. When the reorientation angle of the field is 120° it is possible to obtain excellent resolution of DNA over the entire range of sizes extending up to 2 megabases, while larger molecules may require a different reorientation angle. At 90°, there is a dramatic increase in the movement of the DNA down the gel and a concomitant loss in resolution At 60° the chromosomes move even faster and none are well resolved.

The pulse times and voltages will vary with the size of the molecules to be resolved, pulse times being longer with larger DNA molecules. Pulse times will generally be in the range of 1 second to several hours, more usually in the range of 5 seconds to 60 minutes. The voltages will generally be in the range of 50 to 400 volts.

Field inversion gel electrophoresis has been applied to the separation of yeast chromosomal DNA. G. F. Carle, N. Frank, and N. V. Olson, Science, 232, 65 (1986). The electric field is periodically inverted so that a single pair of electrodes can be used to generate homogenous electric fields. The reorientation angle is necessarily confined to 180°. While the system produces good resolution of large DNA, with a pattern of separation generally independent of position across the gel, for some pulse times the migration of the DNA is not a monotonic function of size, leading to the unwanted comigration of molecules that differ greatly in size. The problem can only be avoided by choosing an appropriate range of pulse times during electrophoresis.

By comparison, the present invention alternating in orientation with a single pulse time can produce excellent resolution of large DNA. It appears that the monotonic relationship between migration and molecular weight is generally preserved through the use of the present invention. Thus, the physical parameters of field strength, reorientation angle, and pulse time can be varied independently in a controlled manner unlike in the field inversion gel electrophoresis technique.

In the next embodiment, uniform non-alternating configurations are exemplified. The electrophoretic separation of smaller macromolecules, such as DNA of less than 50 kilobases, is most efficiently made using the contour-clamped homogenous electric field of the present invention in a nonalternating configuration.

In the conventional electrophoresis of DNA of less than 50 kilobases, higher voltages can be used to accomplish adequate resolution in a shorter period of time. One disadvantage of this approach, however, is that the migration pattern across the gel is distorted. The DNA molecules migrate more slowly at the edge of the gel than in the center, with the effect most pronounced at smaller molecular weights.

Figure 5:
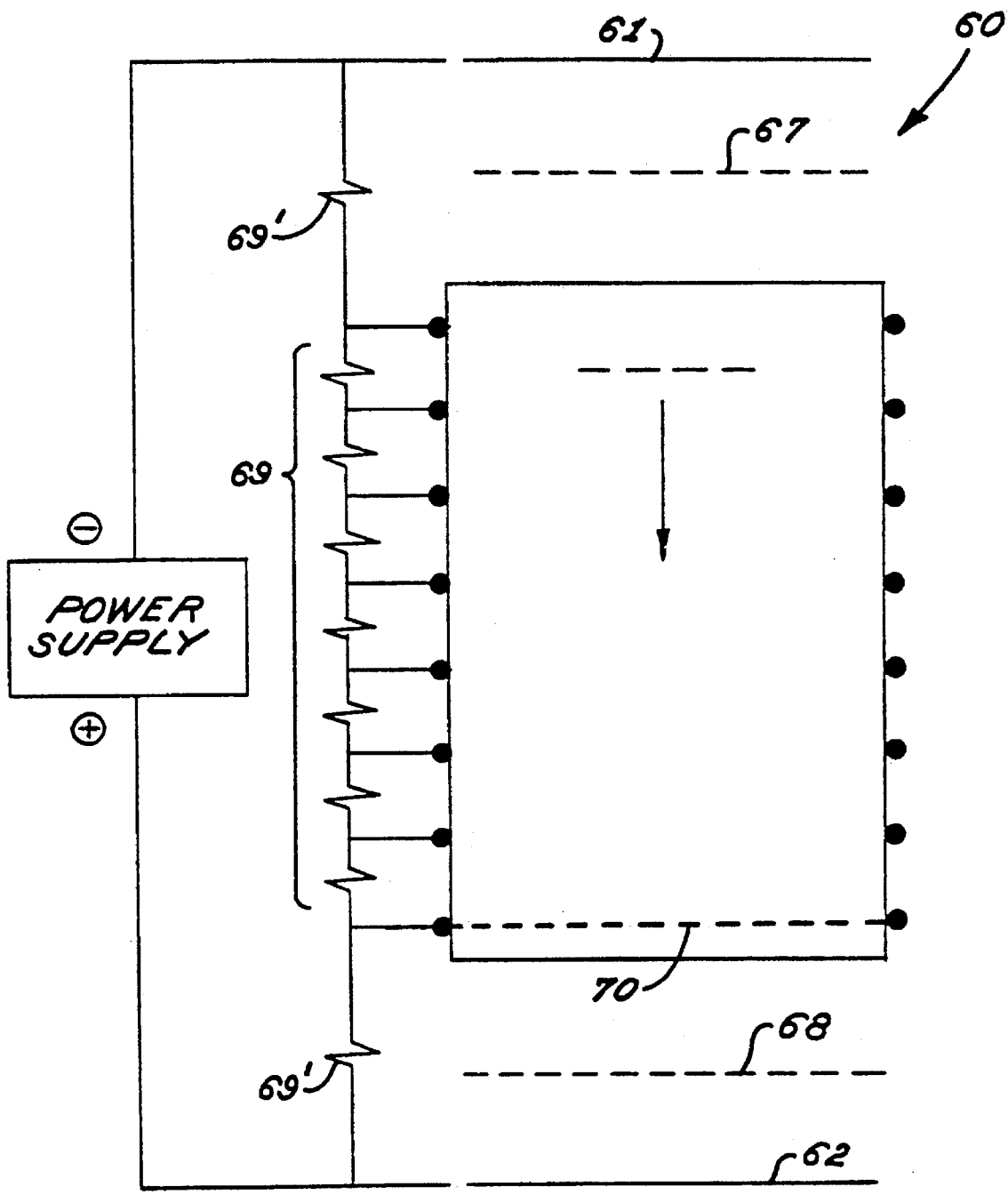
FIG. 5 depicts the apparatus of the present invention for the nonalternating contour-clamped homogenous electric field.

This problem can be eliminated by using the present invention. FIG. 5 shows the modification of a standard horizontal gel apparatus 60 in accordance with the principles of the present invention. The gel and electrode configuration are drawn in appropriate relative proportion. The standard horizontal gel apparatus described in T. Maniatis, E. F. Fritsch, and J. Sambrook, *Molecular Cloning: A Laboratory Manual*, 153 (Cold Spring Harbor Laboratory, 1982), has two main electrodes, the positive 61 and negative 62 electrodes, submerged in wells 63 at the end of the buffer tank 64. The standard apparatus was modified by adding six new intermediate electrodes in two sets 65, 66 oriented perpendicular to the plane of the gel and on the sides of the apparatus joining the main electrodes 61, 62. The electrode array defines a closed contour surrounding the gel. In a buffer tank of uniform depth, the equivalent electric field would be generated by electrodes substantially closer to the ends of the gel. This equivalent electrical position is indicated by the broken lines 67, 68 in FIG. 5 to give an indication of the contour geometry. The electric field is controlled by clamping the electrodes to potentials through a series of variable resistors 69, 69' connected across the main electrodes 61, 62. It will be understood from the dashed line 70 connecting the lower pair of terminals, that each corresponding pair is interconnected so that the same potential is clamped at equivalent positions on both sides of the gel. In the illustrated apparatus, a uniform field was created by utilizing resistors of 960 ohms for the resistor 69' and 470 ohms for each of the resistors 69. Use of this device allows for the high resolution, nondistorted separation in a short period of time of particles at high voltage.

In the next embodiment, the use of nonuniform nonalternating fields is exemplified. By changing the values of the resistors connecting the electrodes along the contour, this device may be altered to generate any desired field strength gradient in appropriate circumstances.

A negative field strength gradient (i.e. one in which the magnitude of the electric field is less near the $\phi_1$ driving electrodes than near the $\phi_2$ driving electrodes) produces a number of effects on the migration of the DNA. First, the mobility of the DNA decreases as it moves through the gel. Electrophoresis can be prolonged without losing the smaller DNA molecules, thus permitting increased resolution of the larger DNA. Second, the negative gradient counteracts band broadening, with the benefit most pronounced for low molecular weight species. Band broadening is the result of multiple factors, including diffusion, convective flows induced by uneven heating, and eddy migration caused by the multiplicity of migration routes through the gel stabilizer. A suitably strong negative field gradient will focus the band because the leading edge of the band is subjected to a weaker electromotive force than the trailing edge. Third, the migration of the DNA takes a curvilinear trajectory with a progressive increase in the width of the lanes down the gel. The incorporation of a negative gradient in electric field strength necessarily introduces a divergence in the field direction. Thus there are two possible applications of negative field strength gradients: a weak gradient adjusted to counteract band broadening can improve resolution; a strong gradient adjusted to keep small DNA molecules on the gel can provide more time to separate larger molecules on the same gel. The effect of a controlled negative field gradient will be demonstrated in Example 3 below. The use of negative, zero, and positive gradients in electric field strength are also described in an article by Chu et al. entitled "Separation of Large DNA Molecules by Contour-Clamped Homogeneous Electric Fields", *Science* (1987–1986) 234:1582–1585.

The present invention thus provides a means whereby large macromolecules can be separated without distortion with a contour-clamped homogenous electric field in alternating orientations, smaller macromolecules can be separated without distortion even at high voltage with a nonalternating contour-clamped homogenous electric field, and either decreased band broadening or differential resolution can be achieved with a contour-clamped electric field with a negative field gradient.

In the next embodiment, uniform alternating fields of alternating or different field strengths is exemplified. It should be noted that secondary structure in macromolecules such as DNA might also be identified by the method of the present invention. Biological systems can generate DNA molecules in the form of supercoiled circles, nicked circles, branched DNA, and lariats. Such molecules display anomalous mobility shifts with respect to linear DNA in response to voltage changes. The contour-clamped homogenous electric field of the present invention can be used to separate DNA with secondary structure from a mixture of linear DNA. A sample can be run in a homogenous field at one voltage in one dimension and at a different voltage in the other dimension. DNA with secondary structure will appear as spots displaced from the arc of linear molecules. The field orientation can be switched electronically, eliminating the need to manipulate the gel as is done in two dimensional electrophoresis. Furthermore, the field can be switched in intervals, and the run terminated once the desired separation has been achieved. The device in FIG. 1 can be used to achieve the desired effect by the simple modification of adding four equal resistors at the B+ terminals to make the voltage across the B electrodes smaller than that across the A electrodes.

Figure 9A:
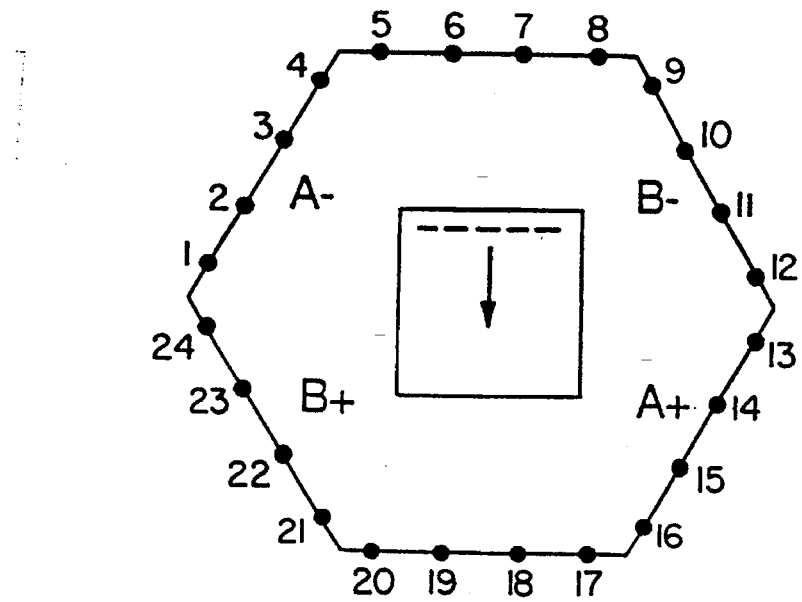
FIGS. 9a through 9c depict a closed contour, and the potentials established at certain corners of the closed contour as the field direction changes.
Figure 9B:
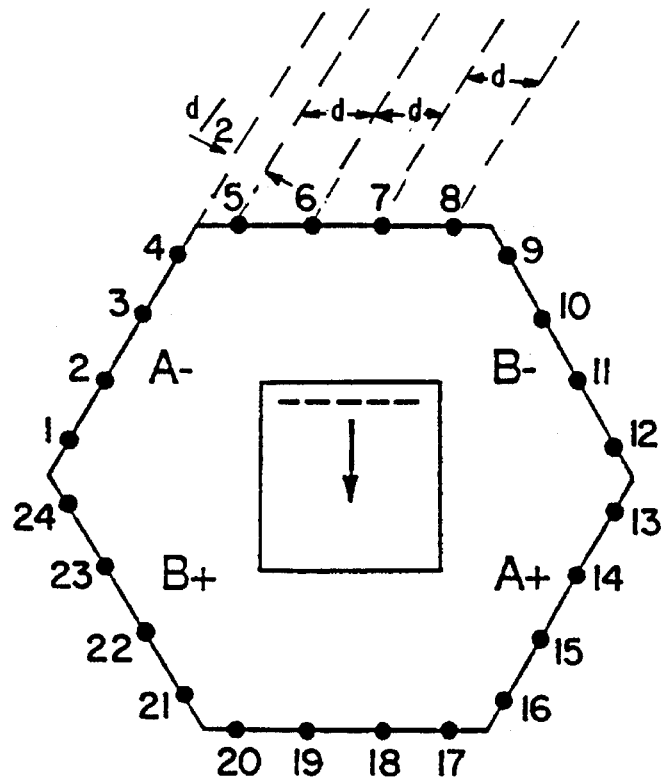
Figure 9C:
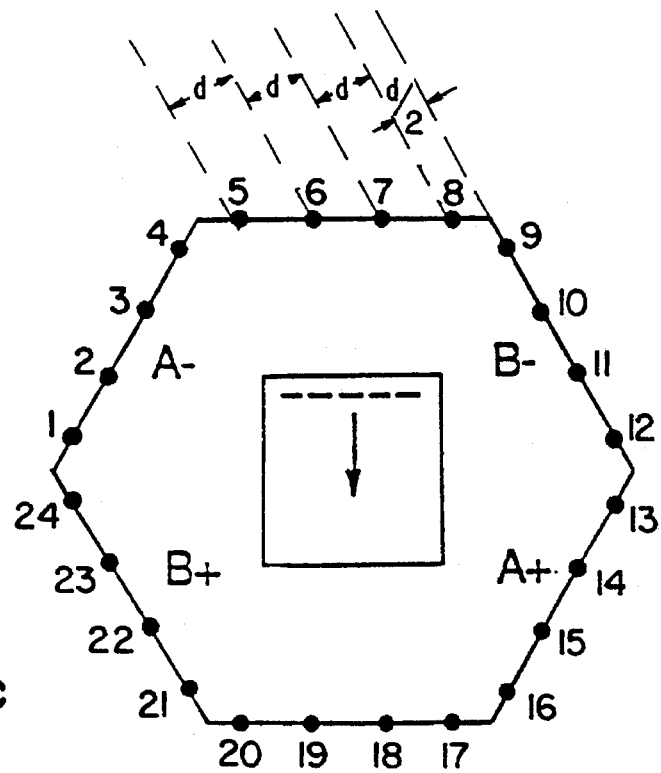

In an alternative embodiment of this invention, the electrode spacing at the corners of the closed contour is fixed to be one half the electrode spacing along the sides of the closed contour. FIGS. 9a–9c depict one embodiment of this invention where a hexagonal closed contour is used, and the perpendicular distance between corner electrode pairs (such as electrode pair 4,5 when the field is oriented perpendicular to the A electrodes, and electrode pair 8,9 when the field is oriented perpendicular to the B electrodes) is one half the perpendicular distance between non-corner electrodes. This arrangement allows more accurate clamping of the electrical potential at the corners of the closed contour.

Figure 10:
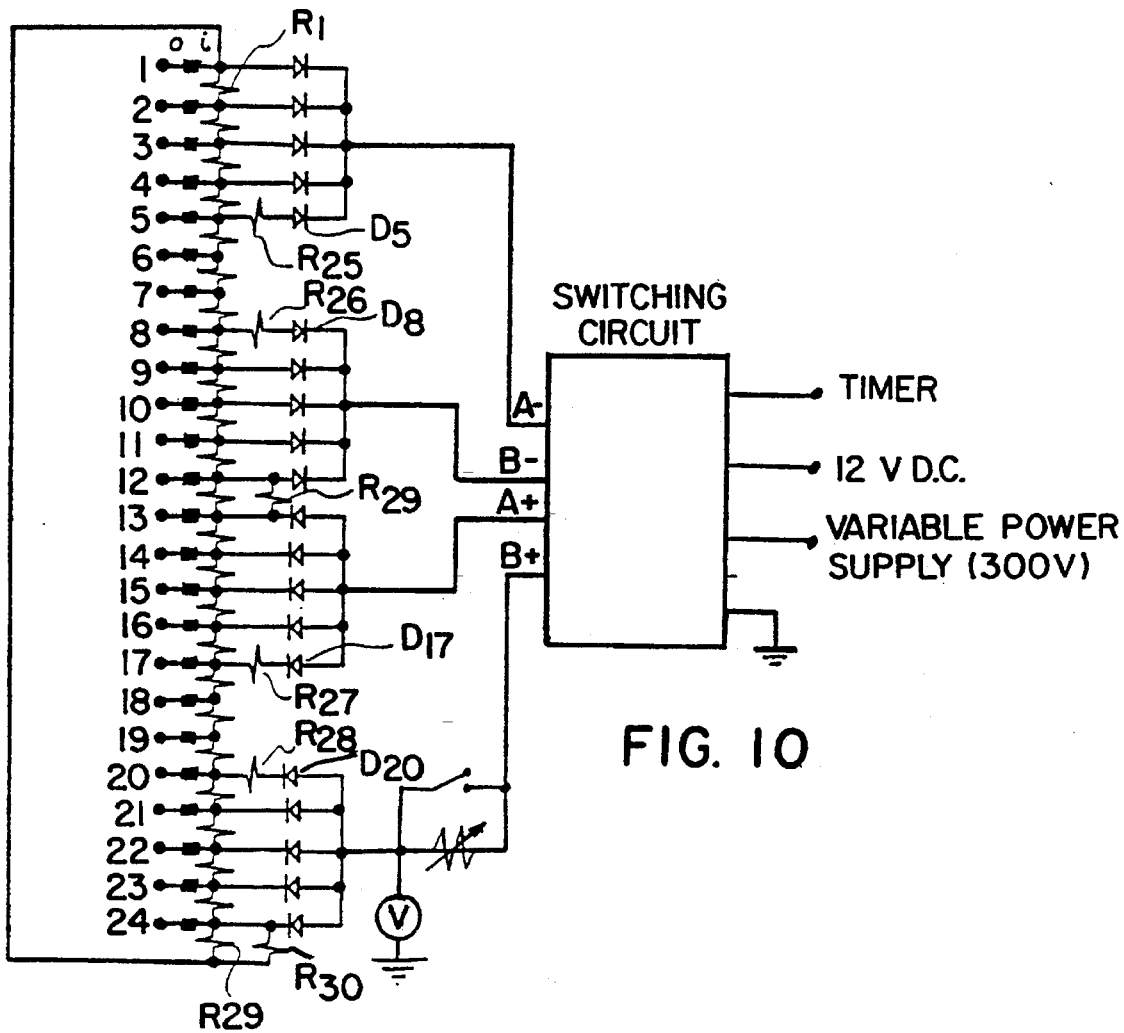
FIG. 10 is a schematic diagram of one embodiment of a circuit for achieving the potentials depicted in FIGS. 9a through 9c.

In one embodiment of the structure of FIG. 9a, as depicted in FIG. 10, the net resistance between corner electrodes switches with field orientation, so that the potential is appropriate for that orientation. To accomplish this, six additional resistors have been added in parallel between the six pairs of corner electrodes. In four cases, resistors R25, R26, R27, and R28 have been added in series with diodes D5, D8, D17, and 20, respectively. This modification causes the potential difference between electrode pairs 4,5; 8,9; 16,17; and 20,21 to change depending on the field orientation. When the A+ and A– electrodes are driving the field, the potential difference between electrode pairs 4,5; and 20,21 drops to half of the potential difference between electrode pairs 8,9; and 16,17. This reflects the fact that the perpendicular distance of electrode 5 from the zero isopotential line formed by the A– electrodes is half the perpendicular distance between adjacent electrodes from electrodes 5 to 12, as shown in FIG. 9b. Conversely, when the B+ and B– electrodes are driving the field, the potential difference between electrode pairs 4,5; and 20,21 appropriately reflects the perpendicular spacing with respect to the B+ and B– electrodes, as shown in FIG. 9c. These potential differences are necessary for the generation of a uniform electric field, since the potential at any of the intermediate electrodes must be proportional to the perpendicular distance from the intermediate electrode to the imaginary line formed by the driving ground electrodes.

Figure 13:
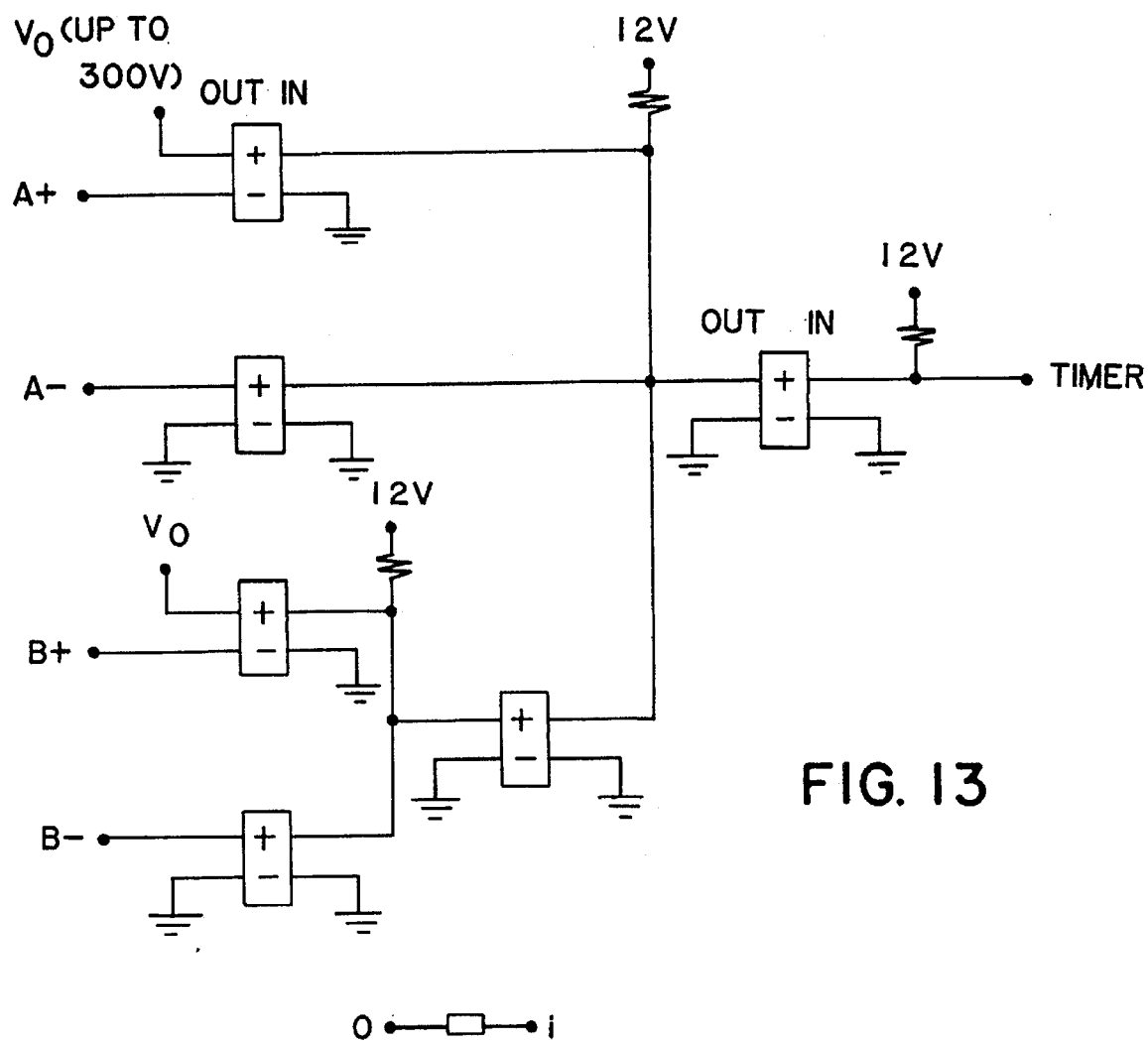
FIG. 13 is a schematic diagram depicting the use of solid state relays in the switching circuit of this invention.

In one embodiment, as shown in the schematic diagram of FIG. 13, solid state relays (such as the Crydon PVR3301) are used as the switching mechanisms, rather than the relay mentioned above. The use of a solid state relay permits more rapid switching, if desired, and provides increased reliability and less audible noise.

Figure 14:
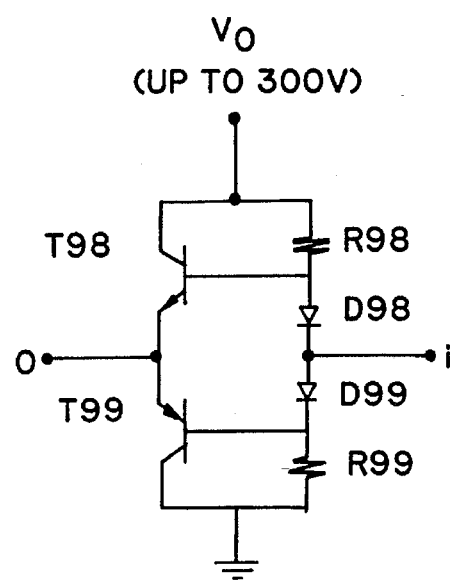
FIG. 14 is a schematic diagram depicting one embodiment of a circuit suitable for driving an electrode of a structure constructed in accordance with the teachings of this invention.

In another embodiment, transistor buffer circuits are used between each electrode and the driving circuitry. As shown in FIG. 11, for example, buffer circuits B1 through B24 are used in order to clamp the electrodes to the appropriate potentials more precisely since the resistance paths between electrodes through the chemical buffer are electrically isolated from the resistive voltage divider, thereby allowing the resistive voltage divider to operate more precisely. Such buffer circuits have relatively high input impedance, so as not to load down the resistor voltage divider, and a relatively low output impedance, so as to provide adequate clamping of the electrodes. It is to be understood that buffer circuits such as buffer circuits B1 through B20 can be used to advantage in any embodiment of this invention. Similarly, it is to be understood that buffer circuits such as buffer circuits B21 through B24 can be used to advantage in any embodiment of this invention. In one embodiment of this invention, such buffers are formed as shown in the schematic diagram of FIG. 14 in which emitter follower pull-up and pull-down transistors T98 and T99 are used, respectively. The gain provided by the transistors allows the voltage dividers formed by the series of resistors to operate more precisely, without being loaded down by large amounts of current flowing through the resistors. In one such embodiment, the following component values are used:

T98 2N3439

T99 2N5416

R98 150K ¼ Watt

R99 150K ¼ Watt

D98 1N4004

D99 1N4004

Figure 11A:
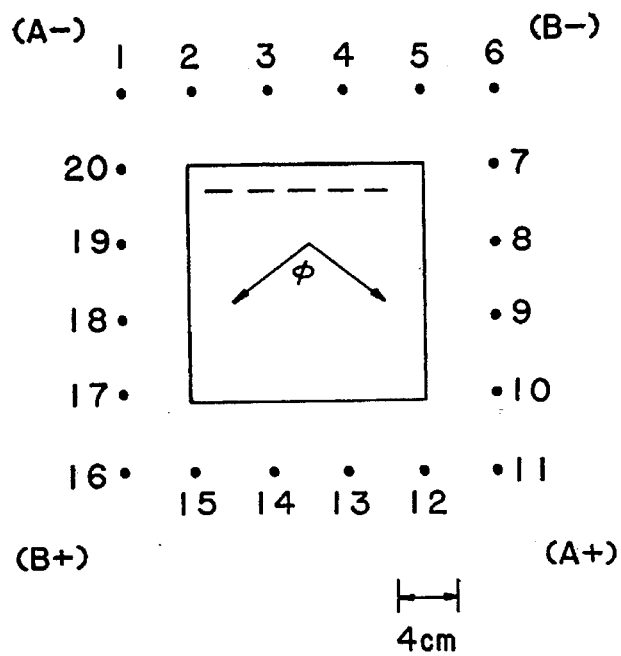
FIG. 11 is a schematic diagram of one embodiment of a circuit suitable for driving the electrodes of a structure constructed in accordance with the teachings of this invention.
Figure 11B:
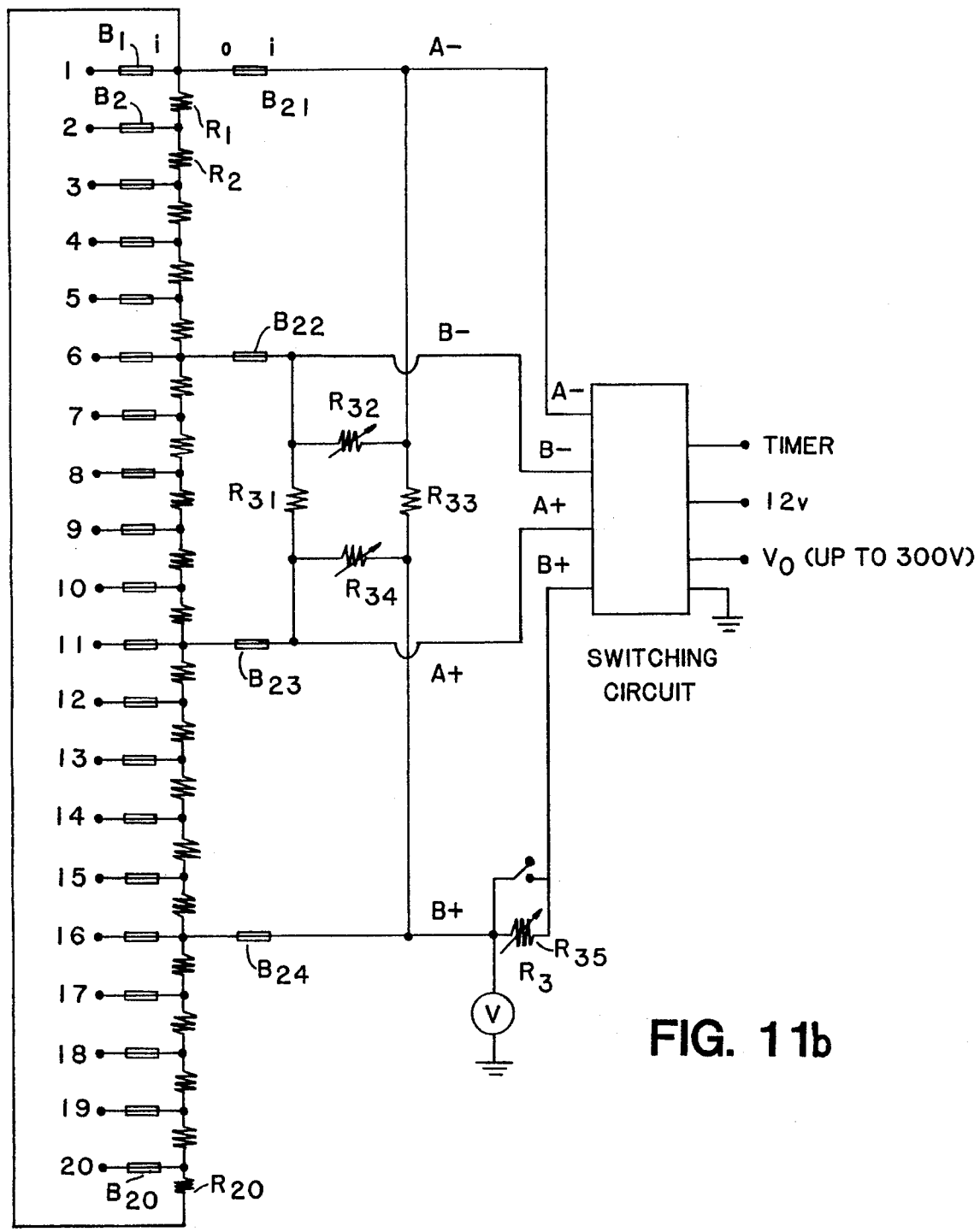

While the above described embodiments allow specific reorientation angles based upon the shape of the closed contour as defined by placement of the electrodes, in an alternative embodiment a structure is provided such that an arbitrary reorientation angle is capable of being provided within a single closed contour. Thus, in accordance with this embodiment, a single apparatus defining a single closed contour can be used to provide any desired reorientation angle. One embodiment of such a structure is depicted in FIG. 11a, in which the reorientation angle is controlled by clamping the corner electrodes to appropriate potentials, for example using the circuit of FIG. 11b. As shown in FIG. 11b, two pairs of resistors R31,R32 (with resistance value $R_i$) and R33,R34 (with resistance value $R_j$). In one embodiment of FIG. 11b,

| $R_1 - R_{20}$ | 2K | ½ W |
| $R_{31}, R_{33}$ | 10K | 2W |
| $R_{32}, R_{34}$ | up to 20K | 2W |

$$\phi = 2\tan^{-1}\left(\frac{R_j}{R_i}\right); \quad (1)$$

where $\phi$ is the reorientation angle.

Figure 12A:
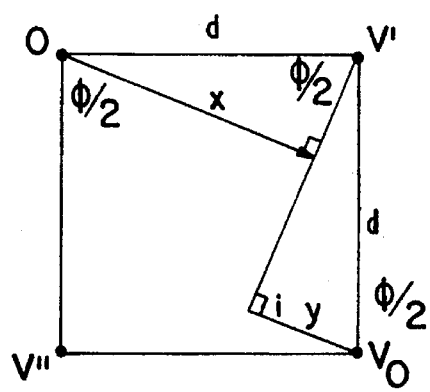
FIG. 12a is a vector diagram and FIG. 12b is a circuit model depicting the action at the corners of the contour of the embodiment of FIG. 11.
Figure 12B:
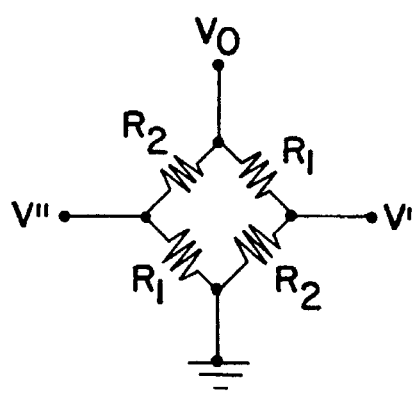

Resistors R31 through R34 act as voltage dividers so that the corner electrodes 1, 6, 11, and 16 are clamped to potentials appropriate for a given electric field orientation. When electrodes 1 and 11 are the driving electrodes (A− and A+), electrodes 6 and 16 are clamped to potentials which fix the orientation angle of the electric field, as shown in FIGS. 12a and 12b.

For a field orientation at an angle ½φ with respect to the vertical (i.e., a reorientation angle of φ between alternating fields), V' should reflect the relative perpendicular distances from the driving electrodes. Those distances are x and y in FIG. 12a, $$x = d \sin(\tfrac{1}{2}\phi) \quad (2)$$

$$y = d \cos\left(\tfrac{1}{2}\phi\right) \quad (3)$$

-continued $$V' = \left[\frac{x}{x+y}\right]V_o \quad (4)$$

$$= \left[\frac{1}{1+\frac{y}{x}}\right]V_o$$

$$= \left[\frac{1}{1+\frac{\cos\left(\tfrac{1}{2}\phi\right)}{\sin\left(\tfrac{1}{2}\phi\right)}}\right]V_o$$

$$= \left[\frac{1}{1+\cot\left(\tfrac{1}{2}\phi\right)}\right]V_o$$

A similar calculation yields $$V'' = \left[\frac{1}{1+\tan\left(\tfrac{1}{2}\phi\right)}\right]V_o \quad (5)$$

The resistive voltage bridge in FIG. 12b produces potentials V' and V'' with the correct relationship:

$$V' = \left[\frac{R_j}{R_i+R_j}\right]V_o \quad (6)$$

$$= \left[\frac{1}{1+\frac{R_i}{R_j}}\right]V_o$$

$$V'' = \left[\frac{R_i}{R_i+R_j}\right]V_o \quad (7)$$

$$= \left[\frac{1}{1+\frac{R_j}{R_i}}\right]V_o$$

Thus, if the angle φ is defined by the relationship, $$\frac{R_i}{R_j} = \cot\left(\tfrac{1}{2}\phi\right) \quad (8)$$

then $$\frac{R_j}{R_i} = \tan\left(\tfrac{1}{2}\phi\right) \quad (9)$$

and substitution of Equations 8 and 9 into Equations 6 and 7 yields expressions for V' and V'' in the form of Equations 4 and 5. Thus, V' and V'' have assumed values which are appropriate to an electric field with orientation angle ½φ, proving the validity of Equation 1.

In another embodiment, as shown in the schematic diagram of FIG. 11b, a variable resistor (typically approximately 20K, 5 watts) is used as resistor $R_{35}$ in the B portion of the electrical circuitry in order to cause a lower potential to be used in the B direction than in the A direction, while using a single voltage source $V_0$. This has the advantage of allowing the structure to be used to, for example, separate DNA on the basis of secondary structure.

In accordance with this embodiment of the invention, solid state relays can be used as described above with regard to FIGS. 10 and 13, and buffer circuits can be used as described above with regard to FIGS. 10 and 14.

The following examples further illustrate the present invention but, of course, should not be construed as in any way limiting its scope.

EXAMPLE 1

This example compares the gel electrophoresis of yeast chromosomal DNA in accordance with the present invention using an alternating electric field with the conventional orthogonal-field-alternation gel electrophoresis (OFAGE) such as is illustrated in G. F. Carle and N. V. Olson, Nucleic Acids Res. (1984) 12:5647.

Chromosomal DNA was prepared from *S. cerevisiae*, strain YNN295 as described in D. C. Schwartz and C. R. Cantor, *Cell.*, 37, 67 (1984), except that the agarose inserts were washed with 50 mM EDTA, pH 8, after detergent and proteinase K treatment. The gels were formed from 35 ml of 1% agarose (Baker standard low electroendosmosis, A426-5) in an electrophoresis buffer 0.5× TBE (45 mM Tris, 45 mM boric acid, and 1.25 mM EDTA, pH 8.3) poured onto a sand blasted glass plate (10.5×10.5×0.2 cm). The molten agarose was confined to the plate by surface tension. Wells in the gel were made with a thin comb (0.030 inches). Agarose inserts containing chromosomal yeast DNA were melted at 65° C. for five minutes and loaded into the wells with a glass micropiper.

The yeast chromosomal DNA was subjected to electrophoresis with: (a) the OFAGE apparatus for 48 hours, (b) the hexagonal array apparatus of the present invention for 24 hours, and (c) the square array configuration of the present invention for 15.5 hours.

The OFAGE apparatus is disclosed in G. F. Carle and N. V. Olson, 1984, supra. The hexagonal array and square array contour-clamped uniform electric field apparati were those depicted in FIGS. 1 and 2 and described above. The electrodes consisted of 0.030 inch diameter platinum wire and were suspended in the buffer. The electrodes were clamped to the appropriate potentials through a series of 470 ohms/2 watt resistors for the hexagonal array and 820 ohms/2 watt resistors for the square array. A GraLab Model 451 digital timer/intervalometer was used to drive the switching relay to generate the electric fields in alternating orientations. The buffer was circulated around the gel, as described in G. F. Carle et al., and cooled to 90° C. by passage through a coil of silicone tubing placed in a Haake A81 water bath.

The gels were run under similar conditions to facilitate comparison: the field was reoriented every 80 seconds and the field strength was 6 volts/cm. In the OFAGE apparatus the electric field strength is nonuniform and was nominally defined as the voltage divided by the perpendicular distance between the electrode pairs.

Following electrophoresis, the gels were stained in 0.5 µg/ml ethidium bromide and photographed. The following bands were identified by Southern blot using specific sequence probes: chromosome II, LYS2; chromosome IV, CEN4; and chromosome XII, GAL2. The chromosome I band was identified on the basis that it has been reported to be the highest mobility band. See, e.g., D. C. Schwartz and C. R. Cantor, *Cell*, 37, 67 (1984), and G. F. Carle and N. V. Olson, *Proc. Natl. Acad. Sci. U.S.A.*, 82, 3756 (1985).

Figure 6C:
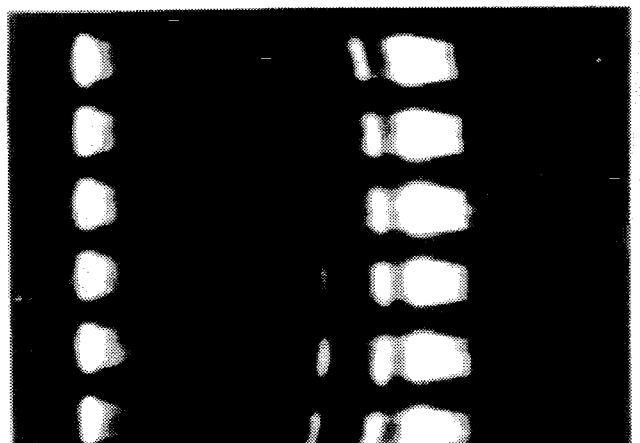
FIG. 6 comprises three photographs showing the separation of yeast chromosomal DNA by: (A) orthogonal-field-alternation gel electrophoresis (Carle and Olson (1984), infra, (B) hexagonal array contour-clamped homogenous electric field electrophoresis, and (C) square array contour-clamped homogenous electric field electrophoresis.
Figure 6B:
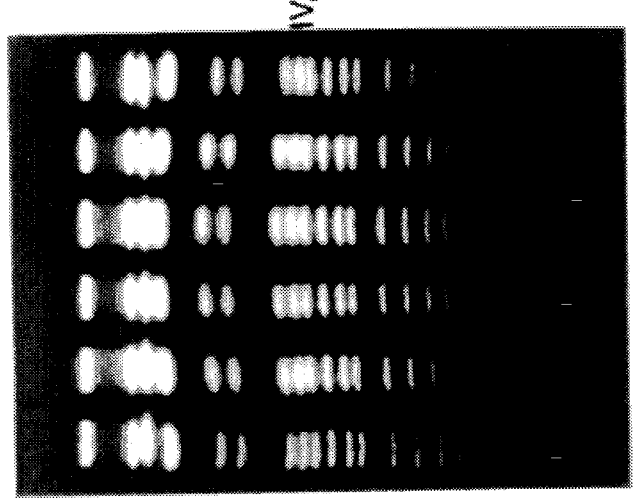
Figure 6A:
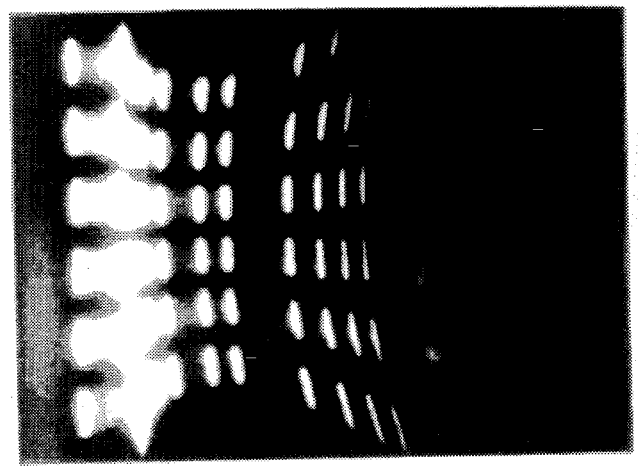

The results of the three electrophoretic separations are set forth in the photographs of FIG. 6. While the conventional technique (see FIG. 6A) and the present invention (FIGS. 6B and 6C) were both capable of separating yeast chromosomal DNA, the pattern of separation resulting through the use of the present invention is quite distinct from that resulting from the use of the OFAGE apparatus. SpeCifically, use of the present invention (see particularly FIG. 6B) led to a pattern of separation which was independent of position across the gel, and thus comparison between multiple samples could be made with confidence through the use of the present invention. The uniformity of separation across the gel using the square array (FIG. 6C) of the present invention was somewhat less than that utilizing the hexagonal array. This is believed to be the result of the potential in the square array being clamped at only four electrodes between the driving electrodes compared to eight such electrodes in the hexagonal array.

Figure 7:
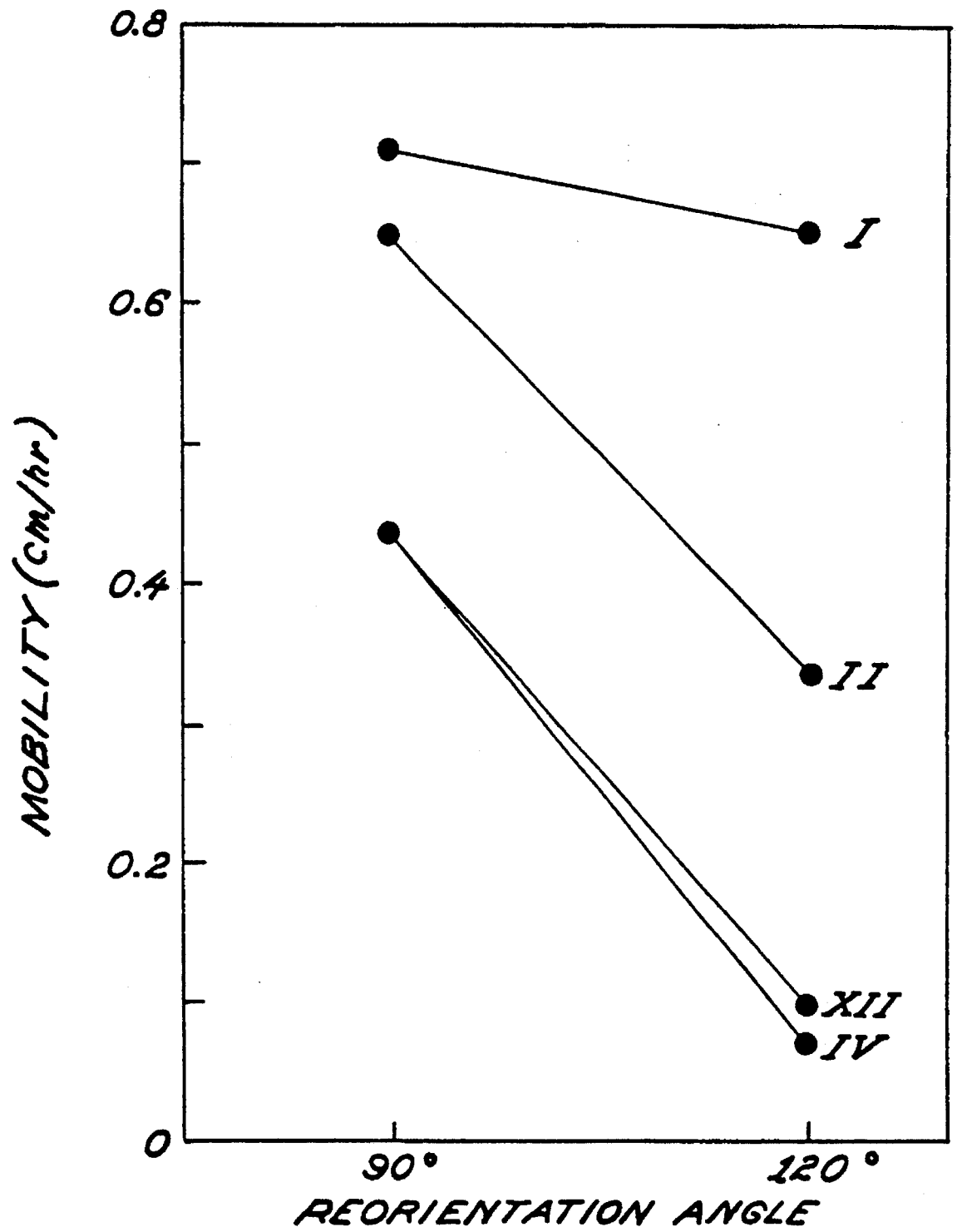
FIG. 7 is a graph showing the mobility of DNA chromosomes I, II, IV and XII as a function of the reorientation angle in the contour-clamped homogenous electric field.

The pattern of chromosome separation changes dramatically with the reorientation angle of the electric field. In the OFAGE apparatus, different parts of the gel are subject to different reorientation angles, mostly in the range of 120° to 150°. In the hexagonal array of the present invention, the angle is 120°, and in the square array, it is 90°. The graph of FIG. 7 displays the mobility of chromosomes I, II, IV and XII as a function of reorientation angle of the electric field. The average mobility was calculated by taking the net migration distance of the bands, multiplying by a correction factor (square root of 2 for the square array, and 2 for the hexagonal array) to compute the true migration distance in the alternating field, and dividing by the running time of the gel. As is apparent from this graph, at 90° there was a dramatic increase in the movement of the DNA down the gel as compared to 120°. Although not shown in the graph, at 60° the chromosomes moved even faster. A comparison of photographs B and C of FIG. 6 involving reorientation angles of 120° and 90°, respectively, demonstrate the lower mobility and concomitant increase in resolution associated with the larger orientation angle.

EXAMPLE 2

This example compares the gel electrophoresis of DNA fragments of varying size in the range of 75 to 12,216 bp (molecular weight markers, Bethesda Research Laboratories 5615 SA/SB) using: (a) conventional apparatus and conditions, (b) conventional apparatus and buffer recirculation, and (c) conventional apparatus modified in accordance with the present invention as described above with buffer recirculation.

The apparatus of FIG. 5 was used with the resistances 69' of 960 ohms and resistances 69 of 470 ohms. The resistances at the ends were about two-fold higher than those in between, reflecting the increased electrical distance between the driving electrodes 61, 62 and the first of the intermediate electrode pairs as shown in FIG. 5. The gels of 0.7% agarose were run in 0.5× TBE containing 0.5 µg/ml ethidium bromide at 7.25 volts/cm for 110 minutes.

It was found that when the apparatus was run in the conventional manner, i.e., with the intermediate electrodes absent, the migration pattern was distorted. When the buffer was recirculated across the top of the gel, there is a redistribution of the uneven heating in the gel and some improvement in the migration pattern; however, distortion was still apparent. In contrast, when the buffer was recirculated and the array of intermediate electrodes was added to generate a contour-clamped homogenous electric field in accordance with the present invention, migration of the DNA was uniform to the very edge of the gel. The present invention in conjunction with the effective heat dissipation resulting from the recirculation of the buffer permitted the rapid resolution of DNA without significant distortion.

EXAMPLE 3

To further demonstrate how controlled contour clamped electric field gradients can effect the electrophoretic separation of DNA, the apparatus of FIG. 5 was again used along with the gel and DNA fragments of Example 2. The resistors connecting the electrodes along the contour, however, were changed to clamp the electrode potentials in a different pattern from that used in Example 2. The resistances from the negative pole 61 to the positive pole 62 were: (a) 820, 390, 330, 270,180, 120, 82, 51, and 100 ohms, (b) 960, 470×7, and 960 ohms, and (c) 100, 51, 82, 120, 180, 270, 330,390, and 820 ohms. The field strength, computed as the slope of the potential curve (a) decreased from 7.76 to 1.0 volts/cm, (b) remained constant at 7.25 volts/cm, and (c) increased from 1.0 to 7.76 volts/cm, respectively, as the DNA moved through the gel. Thus the field strength gradients were negative, zero, and positive, respectively. The gels were run with 200 volts across the driving electrodes for 180, 120, and 200 minutes, respectively.

It was found that the negative field gradient produced a number of effects on the migration of the DNA: the mobility of the DNA decreased as it moved through the gel, band broadening decreased with the effect most pronounced for low molecular weight species and the migration of the DNA took a curvilinear trajectory with a progressive increase in the width of the lanes down the gel.

The results of the use of the zero and positive field gradient gels were included in this example to emphasis the above effects by comparison. As in Examples 1 and 2, the zero gradient produced uniform separation across the gel, but did not separate the larger fragments quite as well as the controlled contour clamped negative gradient. With the positive gradient, the separation of smaller fragments was clearly favored at the expense of larger fragments. Band broadening was exacerbated, especially for smaller molecular weights. Finally, the trajectory of the DNA caused a decrease in the width of the lanes down the gel.

It should be understood that the laboratory devices discussed herein and the particular applications set forth in Examples 1–3 are only specific examples which are convenient for explaining the present invention. Numerous variations are possible and are within the scope of this invention.

Because contour-clamped electric fields can be used to control the electrophoretic separation of DNA in ways not accessible to previous methods, the present invention may have application to a broad range of other problems in the separation of macromolecules.

Although the foregoing invention has been described in some detail by way of illustration and example for purposes of clarity of understanding, it will be obvious that certain changes and modifications may be practiced within the scope of the appended claims.

What is claimed is:

1. An apparatus for electrophoretic separation and detection of particles of a sample using an electric field, said apparatus comprising:

a support for a gel medium in which one or more particles of a sample can be placed;

a plurality of electrodes arranged in a closed contour around said gel medium;

a clamping device simultaneously clamping all of the electrodes arranged in the closed contour at predetermined electrical potentials, thereby establishing an electric field in the gel medium of desired magnitudes and orientations for performing the electrophoretic particle separation and detection.

2. The apparatus of claim 1, wherein said plurality of electrodes includes a first, second and third set of electrodes, and wherein said clamping device clamps the first set of electrodes at a first potential, the second set of electrodes at a second potential and the third set of electrodes at potentials between the first and second potentials.

3. The apparatus of claim 1, wherein said closed contour is a polygon.

4. The apparatus of claim 3, wherein said polygon has only four or six sides.

5. The apparatus of claim 1, wherein said closed contour is a polygon having at least a first, second, third and fourth side, said electrodes including a first, second, third and fourth set located on respectively the first, second, third and fourth sides.

6. The apparatus of claim 5, wherein said clamping device includes a switching device for controlling the electrical potentials of the electrodes so that the electric field in the gel medium switches between two directions.

7. The apparatus of claim 6, said switching device comprising a mechanical relay or a solid state relay.

8. The apparatus of claim 7, said switching device further comprising one or more switching diodes.

9. The apparatus of claim 1, wherein said electrodes includes a plurality of sets of electrodes arranged around said closed contour, said clamping device comprising:

resistors defined as intraset resistors connecting adjacent pairs of electrodes in each set;

resistors defined as interset resistors each connecting an electrode in one set to an electrode in a different set;

an electrical circuit applying different electrical potentials to different and predetermined sets of electrodes, so that the interset resistors connecting said predetermined sets to the remaining sets cause electrical potentials to be applied to said remaining sets.

10. The apparatus of claim 9, wherein said interset resistors connecting the predetermined sets to the remaining sets and intraset electrodes connecting adjacent pairs of electrodes in said remaining sets of electrodes forming voltage dividers to apply potentials to each electrode in the remaining sets so that such potentials are equilibrated to intermediate levels between the different potentials applied to the predetermined sets of electrodes by said resistors.

11. The apparatus of claim 9, wherein said circuit includes a buffer device connected to said predetermined sets.

12. The apparatus of claim 11, wherein said buffer device includes a plurality of buffer circuits, each connected to one of the predetermined sets of electrodes for driving such set.

13. The apparatus of claim 12, wherein said buffer circuits each includes one or more transistors.

14. The apparatus of claim 1, wherein said plurality of electrodes includes a first and a second electrode generally opposite to each other and at least a third and a fourth electrode arranged around the closed contour separating the first and second electrodes, and wherein said clamping device applies to the first electrode a first potential defined as $\phi_1$, to the second electrode a second potential defined as $\phi_2$, and to each of the remaining electrodes a potential $\phi$ defined by $$\phi = y/a \, (\phi_2 - \phi_1) + \phi_1$$

in order to provide within said closed contour a uniform electric field having a direction, where a is the perpendicular distance between a first and a second line, where the first line is perpendicular to said direction of the electric field and passes through the first electrode and where the second line is perpendicular to said direction of the electric field and passes through the second electrode, and y is the perpendicular distance of said remaining electrode to the second line.

15. The apparatus of claim 1, wherein said closed contour is a quadrilateral having four corners, said electrodes including an electrode at each corner of the quadrilateral defining four corner electrodes, wherein each pair of electrodes at adjacent corners of the quadrilateral defines a pair of adjacent corner electrodes, wherein said clamping device further includes four resistors connected to form an input voltage divider circuit, each resistor corresponding to each pair of adjacent corner electrodes, said input voltage divider circuit responsive to potentials applied thereto to apply potentials to two of the corner electrodes, and wherein the resistances of at least some of the four resistors are adjustable so as to adjust the reorientation angle.

16. The apparatus of claim 15, wherein the quadrilateral is a square or rectangle, and wherein one of the four resisters corresponds to a pair of adjacent corner electrodes and the resistor corresponding to the remaining two corner electrodes form a first pair of resisters having substantially the same first resistance value, the remaining two of the four resisters forming a second pair of resisters having substantially the same second resistance value.

17. The apparatus of claim 16, wherein the resisters in one of the two pairs of resisters are adjustable in tandem in resistance value.

18. A method for electrophoretic separation and detection of particles of a sample using an electric field, said method comprising:
providing a support for a gel medium in which one or more particles of a sample can be placed;
providing a plurality of electrodes arranged in a closed contour around said gel medium; and
simultaneously clamping in a clamping step all of the electrodes arranged in the closed contour at predetermined electrical potentials, for establishing an electric field in the gel medium of desired magnitudes and orientations for performing the electrophoretic particle separation and detection.

19. The method of claim 18, wherein said clamping step clamps the electrodes at such potentials that the electric field in the gel medium is nonuniform.

20. The method of claim 19, wherein said clamping step clamps the electrodes at such potentials that the electric field in the gel medium is substantially uniform.

21. The method of claim 20, wherein said clamping step clamps the electrodes at different potentials at two different times such that at a first instant in time, the substantially uniform electric field is in a first direction, and that at a second instant in time, the substantially uniform electric field is in a second direction at an angle to the first direction.

22. The method of claim 21, wherein said angle is substantially 90 or 120 degrees.

23. The method of claim 18, wherein said closed contour is a polygon having at least a first, second, third and fourth side, said electrodes including a first, second, third and fourth set located on respectively the first, second, third and fourth sides, wherein said clamping step applies electrical potentials to the first, second, third and fourth sets such that at a first instant in time, the first direction points from the first set towards the second set, and that at a second instant in time, the second direction points from the third set towards the fourth set.

24. The method of claim 23, wherein at the first instant in time, the clamping step clamps the first set at a higher potential than the second set, and clamps the remaining electrodes including the third and fourth sets at potentials intermediate between those of the first and second sets.

25. The method of claim 23, wherein said clamping step applies electrical potentials to the electrodes so that the electric field in the gel medium alternates between the first and second directions.

26. The method of claim 23, wherein at the second instant in time, the clamping step clamps the third set at a higher potential than the fourth set, and clamps the remaining electrodes, including those in the first and second sets, at potentials intermediate between those of the third and fourth sets.

27. The method of claim 18, wherein said clamping step clamps the electrodes at different potentials at two different times such that at a first instant in time, the electric field is in a first direction with a first strength, and that at a second instant in time, the electric field is in a second direction with a second strength, wherein the first and second directions are at an angle defining a reorientation angle, and wherein said clamping 28. The method of claim 27, wherein said clamping step is accomplished by means of an electrical circuit including resistors, at least one of said resistors being adjustable in resistance value, wherein said clamping step includes adjusting the resistance value of said adjustable resistor to select the reorientation angle.

* * * * *

UNITED STATES PATENT AND TRADEMARK OFFICE
CERTIFICATE OF CORRECTION

PATENT NO. : 5,549,796
DATED : August 27, 1996
INVENTOR(S) : Gilbert Chu et al.

It is certified that error appears in the above-indentified patent and that said Letters Patent is hereby corrected as shown below:

In Column 16, Line 9 in Claim 5
    replace: "side, said electrodes includlng a first, second, third and" with --side, said electrodes including a first, second, third and--

In Column 17, Lines 15, 18, 20 at Claim 16 & Lines 22-23 at Claim 17 replace: "resisters" with --resistors--

In Column 18, Line 39 at Claim 27
    replace: "clamping" with

--clamping step is such that the reorientation angle is adjustable to any predetermined value.--

Signed and Sealed this

Third Day of December, 1996

Attest:

BRUCE LEHMAN

Attesting Officer      Commissioner of Patents and Trademarks

UNITED STATES PATENT AND TRADEMARK OFFICE
CERTIFICATE OF CORRECTION

| | | |
|---|---|---|
| PATENT NO. | : 5,549,796 | Page 1 of 1 |
| APPLICATION NO. | : 08/241063 | |
| DATED | : August 27, 1996 | |
| INVENTOR(S) | : Chu et al. | |

It is certified that error appears in the above-identified patent and that said Letters Patent is hereby corrected as shown below:

In The Specification Under Column 1:

• Please insert at line 10:

-- FEDERALLY-SPONSORED RESEARCH OR DEVELOPMENT
This invention was made with Government support under contract GM021891 awarded by the National Institutes of Health. The Government has certain rights in this invention. --

Signed and Sealed this
Third Day of April, 2012

David J. Kappos
*Director of the United States Patent and Trademark Office*